(12) United States Patent
Gibertoni

(10) Patent No.: US 11,998,234 B2
(45) Date of Patent: Jun. 4, 2024

(54) PERCUTANEOUS INTRODUCER, PARTICULARLY FOR FLEXIBLE DRAINAGE TUBES AND WITH VARIOUS PROFILES

(71) Applicant: REDAX S.P.A., Poggio Rusco (IT)

(72) Inventor: Lucio Gibertoni, Mirandola (IT)

(73) Assignee: REDAX S.P.A., Poggio Rusco (IT)

( * ) Notice: Subject to any disclaimer, the term of this patent is extended or adjusted under 35 U.S.C. 154(b) by 986 days.

(21) Appl. No.: 16/963,458

(22) PCT Filed: Aug. 27, 2018

(86) PCT No.: PCT/EP2018/073040
§ 371 (c)(1),
(2) Date: Jul. 20, 2020

(87) PCT Pub. No.: WO2019/145056
PCT Pub. Date: Aug. 1, 2019

(65) Prior Publication Data
US 2021/0045771 A1    Feb. 18, 2021

(30) Foreign Application Priority Data
Jan. 23, 2018   (IT) ........................ 102018000001649

(51) Int. Cl.
*A61B 17/34*    (2006.01)
*A61B 17/32*    (2006.01)

(52) U.S. Cl.
CPC .... *A61B 17/3415* (2013.01); *A61B 17/32002* (2013.01); *A61B 17/3423* (2013.01);
(Continued)

(58) Field of Classification Search
CPC .... A61B 17/3415; A61B 2017/320028; A61B 17/3417; A61B 17/3476; A61B 17/3496;
(Continued)

(56) References Cited

U.S. PATENT DOCUMENTS 3,856,009 A * 12/1974 Winnie .............. A61B 17/3401
604/530
5,772,678 A *  6/1998 Thomason ......... A61B 17/3417
604/164.1
(Continued)

FOREIGN PATENT DOCUMENTS

WO    2017211493 A1    12/2017

OTHER PUBLICATIONS

International Search Report dated Oct. 25, 2018 re: Application No. PCT/EP2018/073040, pp. 1-4, citing: US 2017/319232 A1, WO 2017/211493 A, U.S. Pat. No. 5,772,678 A, U.S. Pat. No. 5,843,115 A and US 2014/336581 A1.

(Continued)

*Primary Examiner* — Deanna K Hall
(74) *Attorney, Agent, or Firm* — CANTOR COLBURN LLP

(57) ABSTRACT

A percutaneous introducer, particularly for flexible drainage tubes and with various profiles, includes a main body, the main body having a longitudinally extended tubular element arranged in the distal portion of the main body. The tubular element has a terminal arranged at the distal end of the tubular element. The percutaneous introducer has a sliding body which includes a longitudinally extended obturator arranged in the distal portion of the sliding body, the obturator being inserted and being movable longitudinally within the tubular element of the main body. The obturator includes a cutting blade arranged and fixed at the distal end of the obturator. The percutaneous introducer includes a return and positioning spring adapted to return the cutting blade to a retracted position within its seat, following the controlled exit of the cutting blade through a passage slot arranged in the terminal of the tubular element.

16 Claims, 9 Drawing Sheets

(52) U.S. Cl.
CPC .............. *A61B 17/3496* (2013.01); *A61B 2017/320028* (2013.01); *A61B 2017/3454* (2013.01)

(58) Field of Classification Search
CPC .... A61B 2017/32113; A61B 17/32093; A61B 2017/320052; A61M 25/0662
See application file for complete search history.

(56) References Cited

U.S. PATENT DOCUMENTS

| | | |
|---|---|---|
| 5,843,115 A | 12/1998 | Morejon |
| 2014/0336581 A1* | 11/2014 | Collin .................. A61M 25/065 604/164.08 |
| 2017/0319232 A1* | 11/2017 | Kiev .................. A61B 17/3415 |

OTHER PUBLICATIONS

IT Search Report dated Oct. 18, 2018 re: Application No. 2018000001649, pp. 1-8, citing: US 2017/319232 A1, WO 2017/211493 A, U.S. Pat. No. 5,772,678 A, U.S. Pat. No. 5,843,115 A and US 2014/336581 A1.

Written Opinion dated Oct. 25, 2018 re: Application No. PCT/EP2018/073040, pp. 1-6, citing: US 2017/319232 A1, WO 2017/211493 A, U.S. Pat. No. 5,772,678 A, U.S. Pat. No. 5,843,115 A and US 2014/336581 A1.

* cited by examiner

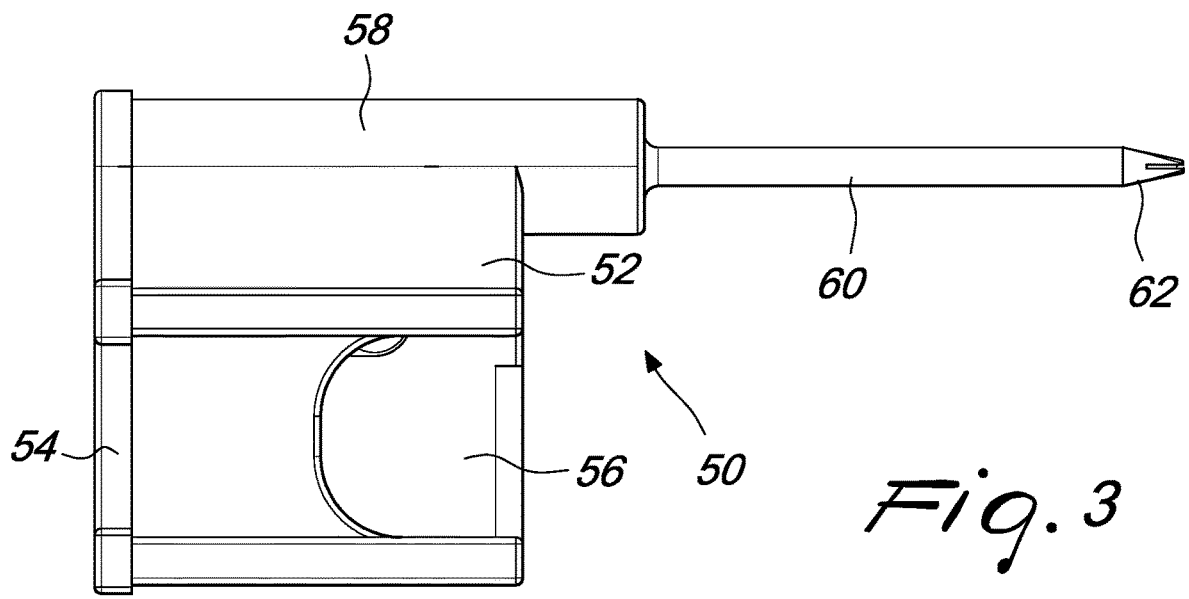
Fig.3
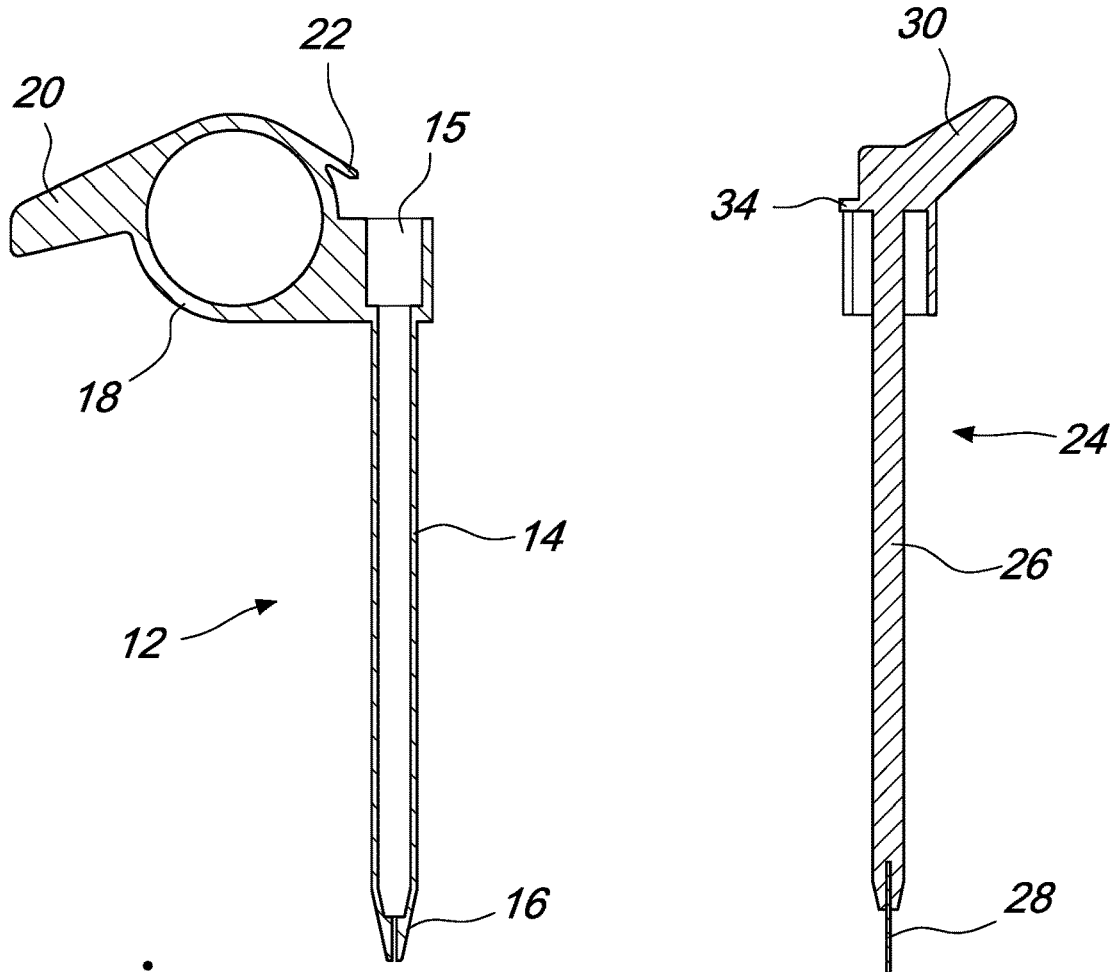
Fig.4
Fig.5

PERCUTANEOUS INTRODUCER, PARTICULARLY FOR FLEXIBLE DRAINAGE TUBES AND WITH VARIOUS PROFILES

TECHNICAL FIELD

The present disclosure relates to a percutaneous introducer, particularly for the introduction in organ tissues of flexible surgical drainage tubes and with various profiles, even different ones from the typical tubular one.

The percutaneous introducer according to the present disclosure is particularly, although not exclusively, useful and practical in the field of thoracic drainage, which has the goal of evacuating fluids, i.e., air and/or liquids, from the thoracic cavity of a patient, in order to avoid the accumulation thereof. Usually, these fluids form as a consequence of traumas and/or surgical procedures.

BACKGROUND

In general, a thoracic surgery drainage tube is a flexible tube provided by using transparent and sterile plastic materials, such as for example PVC (polyvinyl chloride) or silicone, and the tube is inserted, through an incision, in the chest of the patient until it reaches the pleural space in the thoracic cavity, in order to act as a communication pathway toward the outside environment, conveying and evacuating the fluids that have formed.

In particular, the percutaneous insertion of drainage tubes finds its greatest and most frequent applications in situations in which an access to the thoracic cavity is not already available, or in any case in situations in which it cannot be used easily.

As an example, percutaneous insertion of thoracic drainage tubes can occur:
- in the case of emergency/urgency, in the presence of "closed" thoracic traumas, i.e., without communication between the thoracic cavity and the outside environment;
- in the case of iatrogenic pneumothorax or hemothorax, or rather as a consequence of another procedure performed by the physician (such as for example the insertion of a venous catheter through the subclavian vein), which is very frequent in intensive care units;
- as a consequence of surgical procedures performed with mini-invasive methods (such as uniportal VATS); and
- in case of palliative treatment of oncological pleural effusions.

Currently, various types of devices and methods are known for the introduction of a surgical drainage tube in the thoracic cavity of a patient.

Among these known solutions, mention can be made of the so-called trocar catheter, which is composed of a surgical drainage tube made of PVC inside which a metallic obturator is inserted which is meant to give the tube the rigidity that is necessary to insert it through the thoracic wall.

The trocar catheter is available in various versions: closed tip, in which the obturator remains inside the tube; open tip, in which the obturator protrudes from the tip of the tube, maintaining a nontraumatic profile; and sharp tip, in which the obturator protrudes from the tip of the tube with a triangular or tricuspid blade profile.

The first two versions require the physician a more accurate step of incision of the skin and of creation of a passage through the intercostal space. The sharp tip version instead requires only the incision of the skin, after which the physician penetrates the thoracic wall by means of a calibrated thrust.

Moreover, among the above cited known solutions, mention can be made of percutaneous drainages with a small caliber with short-medium permanence, in which access occurs by means of the insertion of a needle which can be of the sharp "cannulated needle" type or of the so-called Verrès type, which is provided with a nontraumatic protection.

In both cases, the surgical drainage tube follows the pathway created by the needle, sliding inside or outside said needle and penetrating inside the thoracic cavity. This type of products is generally characterized by small-caliber drainage tubes, since there is a technical limit to the diameter of the needles that can be used.

In this group of known solutions, drainages that can be positioned with the Seldinger method are also included, i.e., by using a guide wire introduced by means of a needle. The wire, once the needle has been removed, indeed acts as a guide for the insertion of the surgical drainage tube, usually preceded by one or more dilators in order to adapt the dimensions of the access to the dimensions of the tube.

Finally, among the above cited known solutions, mention can be made of small-caliber long-permanence percutaneous drainages, in which positioning is performed exclusively with the Seldinger method and provides for the "tunneling" of the surgical drainage tube in order to reduce the risk of onset of infections.

So-called "tunneling" includes making the surgical drainage tube pass through a subcutaneous portion, typically between 5 and 8 cm long, before it enters the thoracic cavity.

However, known solutions are not free from drawbacks, which include the fact that the perforation of the skin of the patient is highly traumatic. This drawback is particularly relevant in trocar catheters, since the presence of the internal obturator and the generous diameter that is usually used cause a large wound and often also a laceration of the muscle bundles that lie below the skin. Even in the other known solutions, in particular those that use the Seldinger method, dilators are used, since the needle that performs the first perforation is usually much smaller than the surgical drainage tube to be positioned.

Another drawback of known solutions resides in that they use unprotected sharp instruments. This drawback relates to all types of known solutions described previously. In trocar catheters, in fact, the sharp tip version, which has an end with a sharp profile, is widely used. In other types of drainage, needles of various calibers are often used without any form of protection once they have penetrated. In almost all cases, it is necessary to proceed with a preliminary incision of the skin with a scalpel, in order to facilitate the penetration of the surgical drainage tube. Clearly, all this increases the risks for the patient and for the physician during use.

A further drawback of known solutions resides in that it is necessary to apply intense pressure in order to achieve penetration in the chest of the patient. This drawback is particularly significant in trocar catheters, since the crossing of the thoracic wall entails the dilation and/or cutting of muscle bundles. In many cases this pressure causes damages to the patient, to the point of even severe damage to internal organs due to the inability of the physician to reduce the pressure in time after passing through the thoracic wall.

Another drawback of known solutions is the fact that they use completely different positioning methods depending on the type of drainage. The different configuration of the products in fact forces the physician to learn positioning techniques that are very different from each other, extending the learning curve and requiring great specialization.

A further drawback of known solutions resides in that they require great dexterity and specialization of the medical personnel. Due to what has been mentioned above regarding the possible side effects of incorrect maneuvers and of the different positioning methods, the medical personnel that inserts the drainages being considered must have specific training Therefore, the availability of personnel qualified for these operations is a problem from organizational point of view.

Moreover, a drawback of known solutions resides in that they are limited, by their nature, to the use of drainage tubes that have a tubular profile and are made of rigid and semirigid materials. These characteristics are necessary in order to be compatible with the use of the introduction instruments such as trocar obturators, cannulated needles, Verrès needles, dilators, guide wires, and so forth. Therefore, the known solutions are often inadequate for positioning soft tubes, which would be more advantageous for the patient, in particular in the case of long permanences. Moreover, known solutions are completely inadequate for drainage tubes with profiles other than the tubular one, preventing the insertion of other profiles, such as for example the splined one, which is becoming very widespread in surgery.

SUMMARY

The aim of the present disclosure is to overcome the limitations of the background art described above, by devising a percutaneous introducer, particularly for flexible drainage tubes and with various profiles, that allows both the creation of a percutaneous access in a simple, safe and economic manner and the introduction and correct positioning of drainage tubes having different profiles and made of different materials.

Within this aim, the present disclosure provides a percutaneous introducer, particularly for flexible drainage tubes and with various profiles, that allows access through the skin and to the underlying tissues, in particular through the thoracic wall, by means of a blade that is always protected and the cutting action of which is clearly determined (controlled time and depth of exit) and constant.

The present disclosure also provides a percutaneous introducer, particularly for flexible drainage tubes and with various profiles, that allows to avoid operations for dilating the created percutaneous access and therefore to avoid consequent efforts during the positioning of the surgical drainage tube.

The present disclosure provides a percutaneous introducer, particularly for flexible drainage tubes and with various profiles, that allows to not apply any intense pressure during the entry phase through the thoracic or abdominal wall.

The present disclosure also provides a percutaneous introducer, particularly for flexible drainage tubes and with various profiles, that allows to avoid the risk of accidental damage to patients caused by unprotected sharp objects.

The present disclosure further provides a percutaneous introducer, particularly for flexible drainage tubes and with various profiles, that can be used to insert drainage tubes with multiple diameters, profiles and/or different materials, being particularly suitable for the positioning of drainage tubes with profiles different from the tubular one (for example flat profile, splined profile, etc.) and made of soft and nontraumatic materials (for example medical silicone).

The present disclosure provides a percutaneous introducer, particularly for flexible drainage tubes and with various profiles, that allows to use the same method to introduce different types of drainage tubes and in any clinical situation (for example emergency, post-surgical treatment, etc.).

The present disclosure further provides a percutaneous introducer, particularly for flexible drainage tubes and with various profiles, that is suitable to be used in any clinical situation and does not require specialized personnel and/or personnel belonging to the surgical area.

The present disclosure also provides a percutaneous introducer, particularly for flexible drainage tubes and with various profiles, that is highly reliable, relatively simple to provide and at competitive costs if compared with the prior art.

This aim, as well as these and other advantages which will become better apparent hereinafter, are achieved by providing a percutaneous introducer, particularly for flexible drainage tubes and with various profiles, comprising a main body, said main body comprising a longitudinally extended tubular element arranged in the distal portion of said main body, said tubular element comprising a terminal arranged at the distal end of said tubular element, characterized in that it comprises a sliding body which comprises a longitudinally extended obturator arranged in the distal portion of said sliding body, said obturator being inserted and being movable longitudinally within said tubular element of said main body, said obturator comprising a cutting blade which is arranged and fixed at the distal end of said obturator, and in that it comprises a return and positioning spring adapted to return said cutting blade to a retracted position within its seat, following by the controlled exit of said cutting blade through a passage slot arranged in said terminal of said tubular element.

BRIEF DESCRIPTION OF THE DRAWINGS

Further characteristics and advantages of the disclosure will become better apparent from the description of a preferred but not exclusive embodiment of the percutaneous introducer, particularly for flexible drainage tubes and with various profiles, according to the disclosure, illustrated by way of nonlimiting example with the aid of the accompanying drawings, wherein:

FIG. 3 is a lateral elevation view of a second embodiment of the percutaneous introducer, particularly for flexible drainage tubes and with various profiles, according to the present disclosure;

FIGS. 4 and 5 are longitudinal sectional views of the main body and of the sliding body, respectively, of the first embodiment of the percutaneous introducer, particularly for flexible drainage tubes and with various profiles, according to the present disclosure, shown in FIG. 1;

DETAILED DESCRIPTION OF THE DRAWINGS

Figure 1:
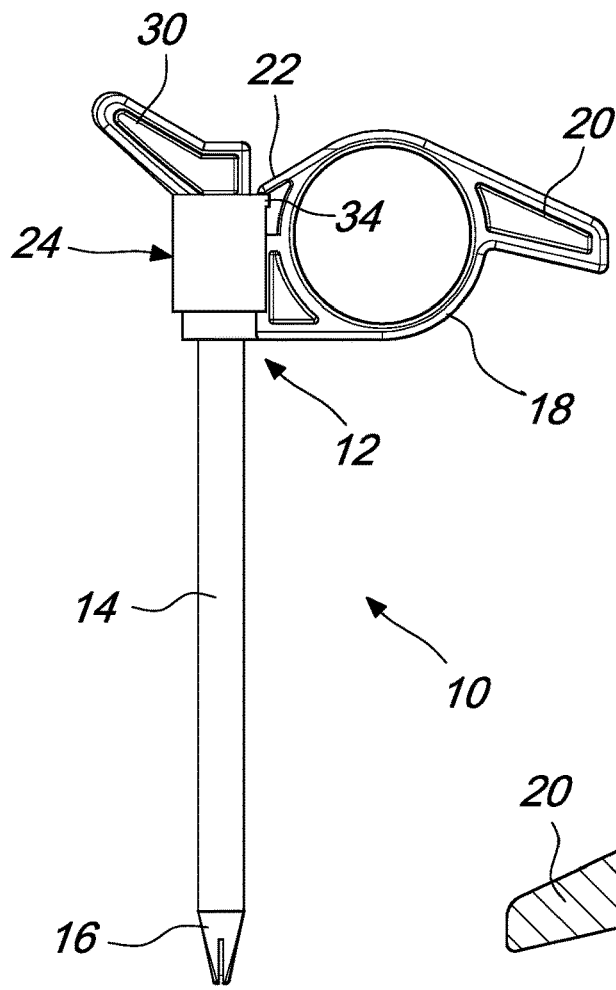
FIG. 1 is a lateral elevation view of a first embodiment of the percutaneous introducer, particularly for flexible drainage tubes and with various profiles, according to the present disclosure.
Figure 2:
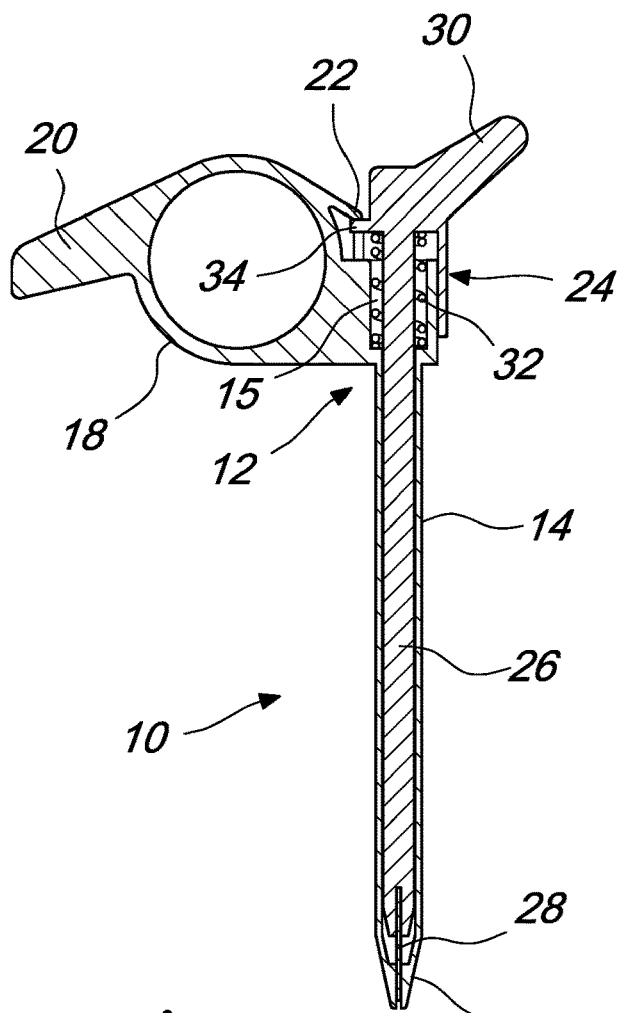
FIG. 2 is a longitudinal sectional view of the first embodiment of the percutaneous introducer, particularly for flexible drainage tubes and with various profiles, according to the present disclosure, shown in FIG. 1.

With reference to FIGS. 1, 2, 4 and 5, a first embodiment (with manual insertion) of the percutaneous introducer, particularly for flexible drainage tubes and with various profiles, according to the disclosure, generally designated by the reference numeral 10, substantially comprises a main body 12, a sliding body 24 and a return and positioning spring 32.

The main body 12 comprises a longitudinally extended tubular element 14, which is arranged at the distal portion of the main body 12. The tubular element 14 comprises a terminal 16, which is arranged at the distal end of said tubular element 14 and is preferably shaped like a recorder mouthpiece. The tubular element 14 can have different diameters depending on the dimensions of the drainage tubes to be introduced.

The tubular element 14 can be integrated in the main body 12. Advantageously, the tubular element 14 can be provided separately and then fixed to the rest of the main body 12 by adhesive bonding or heat-sealing. In this manner it is possible to adopt drainage tubes of different diameters simply by assembling a tubular element 14 of a different diameter.

The main body 12 comprises a ring 18, which is arranged at the proximal portion of the main body 12. The ring 18 is associated with the proximal end of the tubular element 14. The ring 18 is adapted to accommodate a finger, preferably the index finger, of the hand of a physician.

The main body 12 comprises a wing 20, which is associated with the ring 18 and is arranged on the opposite side with respect to the tubular element 14. The wing 20 is shaped so as to be able to grip a finger, preferably the middle finger, of the same hand, giving stability to the grip of the percutaneous introducer 10 by a physician.

The main body 12 comprises a flexible wing 22, which is associated with the ring 18 and is arranged on the same side of the tubular element 14. The wing 22 is adapted to lock the sliding body 24 to the main body 12, preventing its exit during use of the percutaneous introducer 10. In particular, the wing 22 engages a portion of the sliding body 24, preferably at a stroke limiting raised portion 34.

The sliding body 24 comprises an obturator or plunger element 26 which is longitudinally extended and is arranged at the distal portion of the sliding body 24. The obturator 26 is inserted within the cavity 15 of the tubular element 14 of the main body 12. The obturator 26 is movable, in particular it slides longitudinally, within the cavity 15 of the tubular element 14 of the main body 12.

The obturator 26 comprises a cutting blade 28, which slides integrally with the obturator 26 and is arranged and fixed at the distal end of the obturator 26. The cutting blade 28 passes through a passage slot which is arranged at the terminal 16 of the tubular element 14 of the main body 12. The cutting blade 28 is preferably made of stainless steel and is appropriately contoured.

The sliding body 24 comprises a pusher pin 30, which is arranged at the proximal portion of said sliding body 24. The pusher pin 30 is associated with the proximal end of the obturator 26. The pusher pin 30 is shaped so that it can be pressed by a finger, preferably the thumb, of the hand of a physician.

The pressure of the pusher pin 30 causes the exit of the cutting blade 28 through the passage slot of the terminal 16, for an extent that is limited by the stroke limiting raised portion 34, every time the physician needs to do so in order to insert a surgical drainage tube in the chest or in the abdomen of a patient.

The play between the main body 12 and the sliding body 24, in particular the coaxial sliding motion of the obturator 26 of the latter within the tubular element 14 of the former, is adjusted by the return and positioning spring 32. The return and positioning spring 32 is adapted to return the cutting blade 28 to a retracted position inside its own seat (initial "rest" or safety position), following the controlled exit of said cutting blade 28 through the passage slot of the terminal 16.

The operation of the first embodiment (with manual insertion) of the percutaneous introducer, particularly for flexible drainage tubes and with various profiles, according to the disclosure, generally designated by the reference numeral 10, is described as follows.

Initially, the physician grips the percutaneous introducer 10, which is designed to be used with a single hand, leaving to the other hand the task of keeping the cutting end oriented.

In particular, the physician grips the main body 12, inserting the index finger in the ring 18 and positioning the middle finger on the wing 20, which allows a firm and secure grip.

In order to create the percutaneous access by means of the percutaneous introducer 10, initially the terminal 16 of the tubular element 14 of the main body 12 is arranged in contact with the skin of the patient, at the insertion site that has been prepared beforehand by creating the local anesthesia and sterility conditions.

The physician applies a gentle pressure, pressing with his thumb on the pusher pin 30 of the sliding body 24, and slides said sliding body 24, in particular the obturator 26, forward towards the skin of the patient.

The obturator 26 accompanies integrally the cutting blade 28, making it exit by a short extent through the passage slot of the terminal 16, cutting the skin and/or the muscle bundles. The extent of the protrusion of the cutting blade 28 is limited by the stroke limiting raised portion 34.

The advancement movement of the sliding body 24 compresses the return and positioning spring 32, which therefore returns the cutting blade 28 to a retracted position within its own seat (initial "rest" or safety position) as soon as the physician releases the pusher pin 30 of the sliding body 24.

The described operation makes it possible to obtain a calibrated cut of the tissues of the patient that are in front of the percutaneous introducer 10, in particular in contact with the terminal 16. The cut allows the percutaneous introducer 10 to penetrate by a certain extent through the thoracic or abdominal wall of the patient, without the need for further accessories and without having to apply excessive pressure.

The operation can be repeated multiple times at the physician's discretion: every time the physician encounters a certain resistance in the introduction of the device, he can use the cutting blade 28 to cut the underlying tissues and continue the stroke without resistance. Once the percutaneous access has been created, the physician can proceed with the insertion of the surgical drainage tube and with subsequent fixation.

Figure 6:
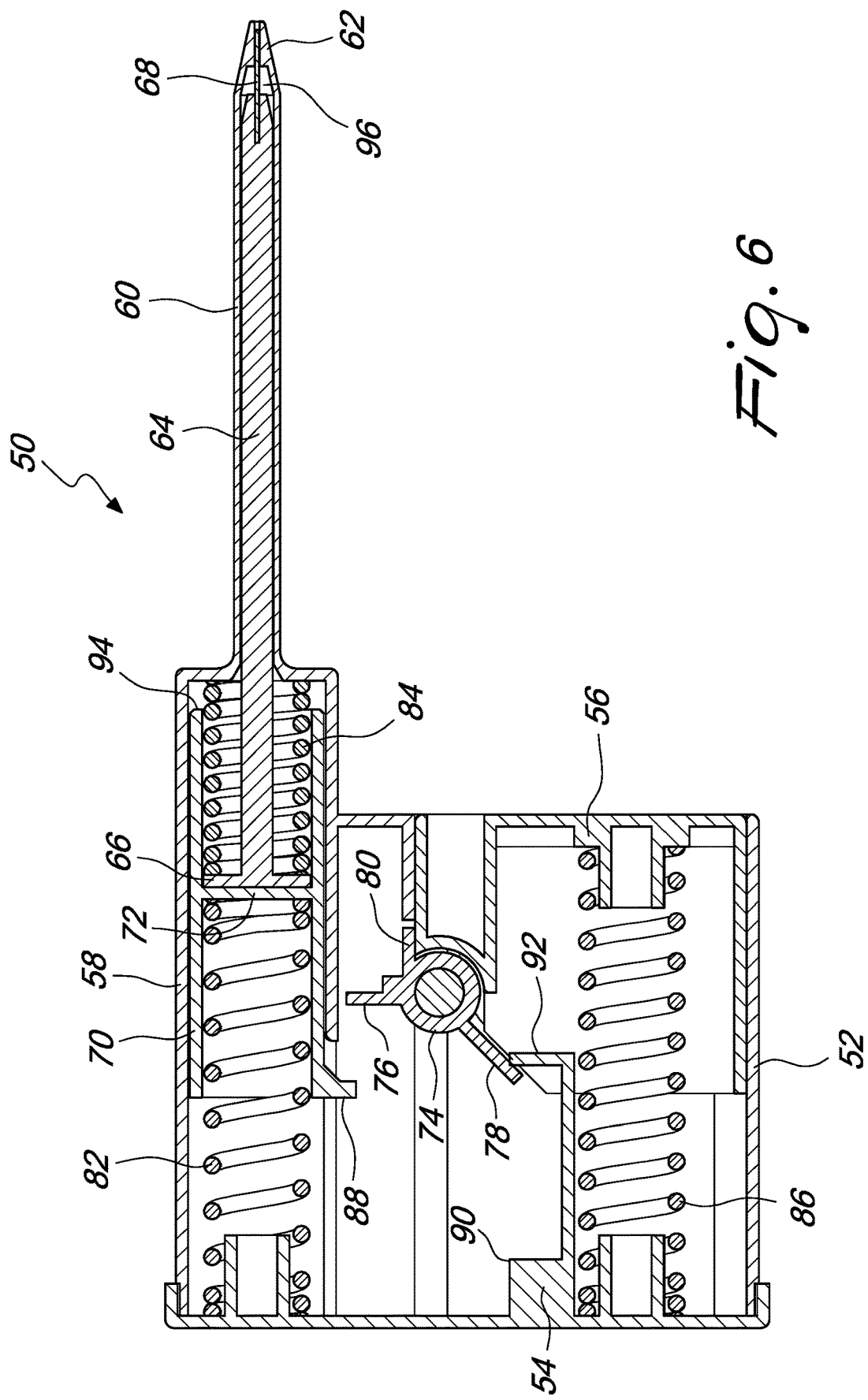
FIGS. 6 to 10 are longitudinal sectional views of the subsequent steps of operation of the second embodiment of the percutaneous introducer, particularly for flexible drainage tubes and with various profiles, according to the present disclosure, shown in FIG. 3.
Figure 7:
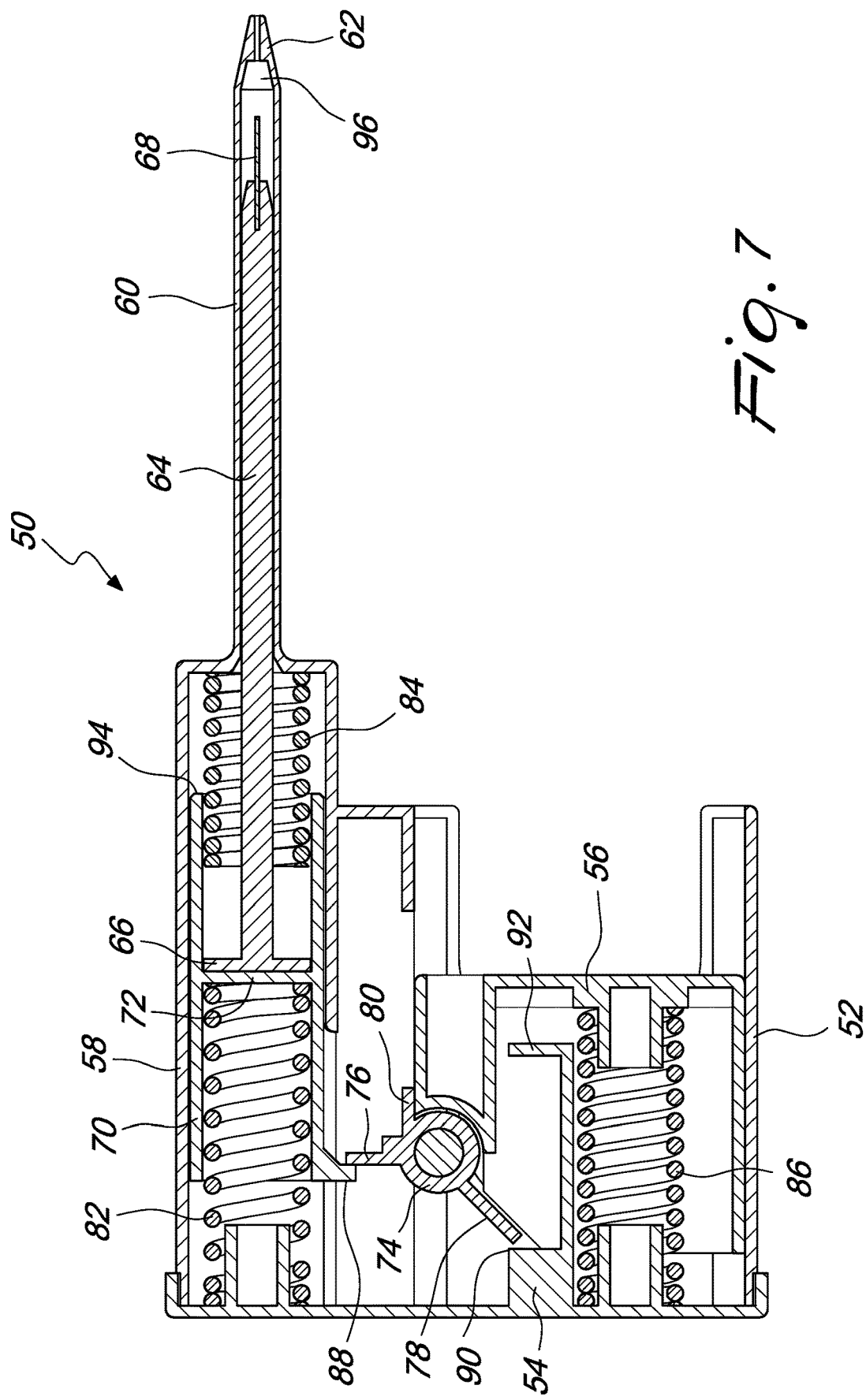
Figure 8:
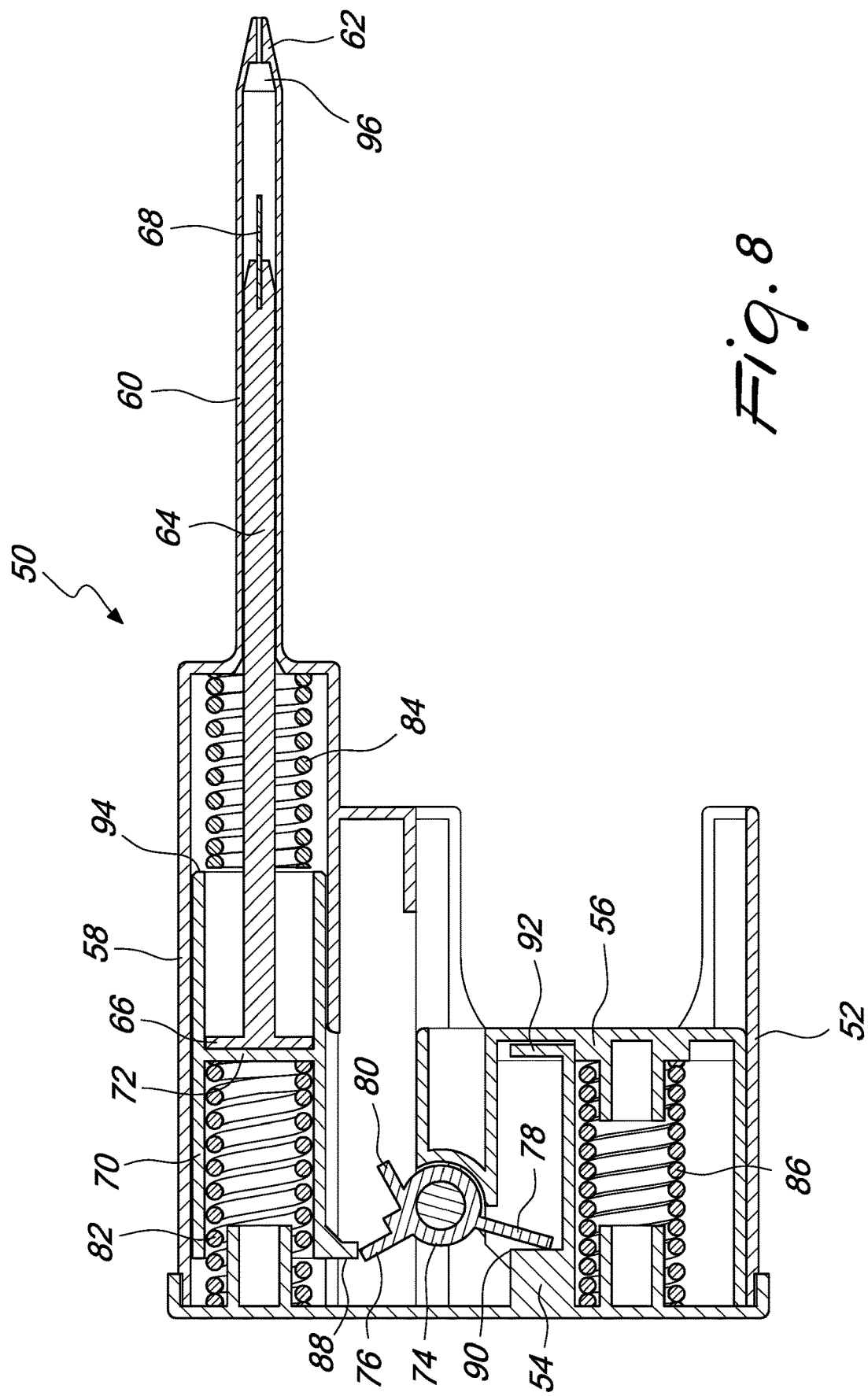
Figure 9:
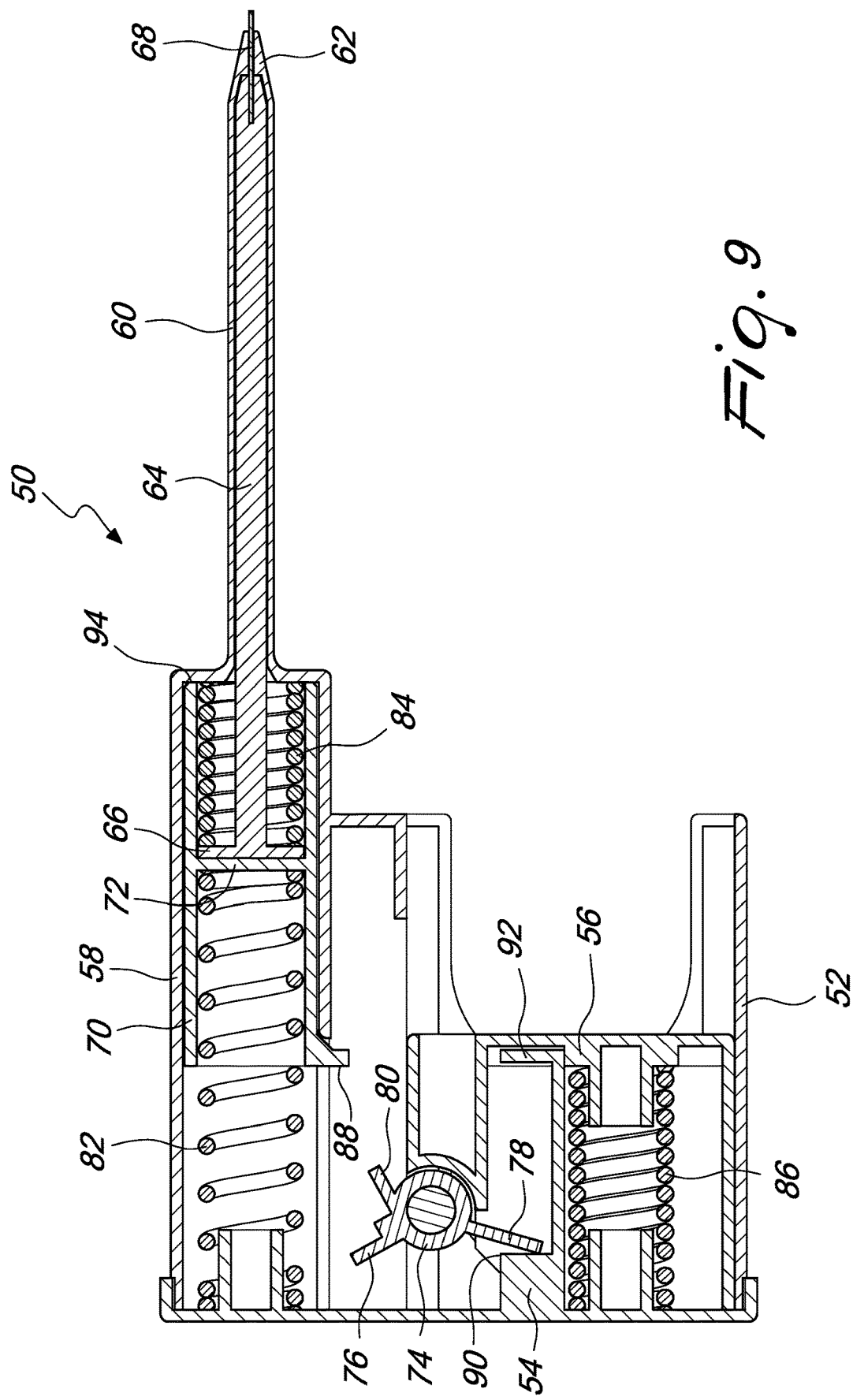
Figure 10:
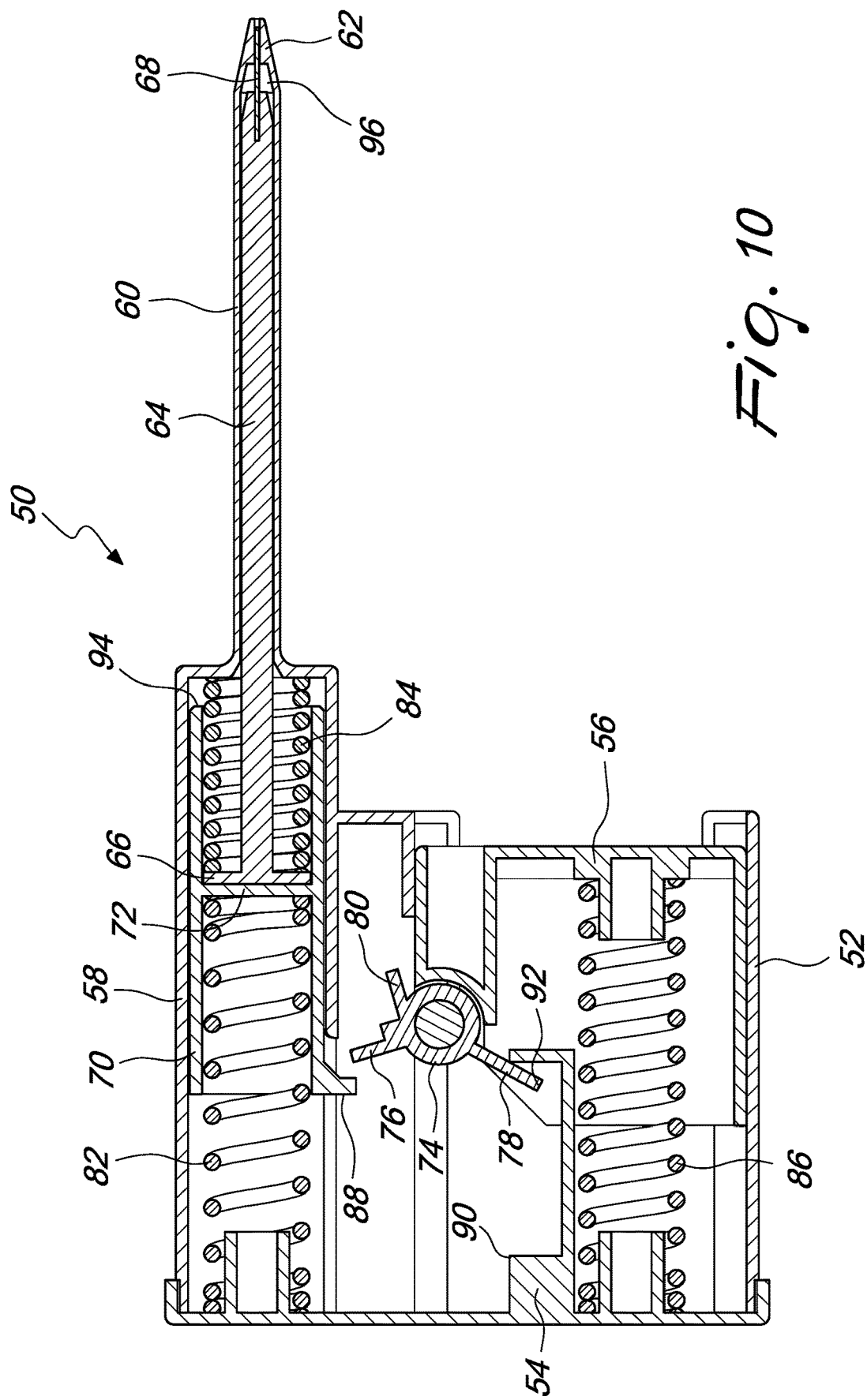

With reference to FIGS. 3 and 6, a second embodiment of the percutaneous introducer, particularly for flexible drainage tubes and with various profiles, according to the disclosure, designated generally by the reference numeral 50, substantially comprises a main body 52, a lid 54, a sliding carriage 56, a sliding body, and a group of springs. The group of springs comprises a loading and release spring 82, a return and positioning spring 84, and a preloading and return spring 86.

The main body 52 comprises a first opening arranged at the proximal face of said main body 52. This first opening is closed by the lid 54.

The main body 52 comprises a second opening which is arranged at the distal face of said main body 52. This second opening accommodates inside it the sliding carriage 56. The sliding carriage 56 can move, in particular slides longitudinally, within the main body 52.

The main body 52 comprises a longitudinally extended tubular element 60, which is arranged at the distal portion of said main body 52. The tubular element 60 comprises a terminal 62, which is arranged at the distal end of said tubular element 60 and is preferably shaped like a recorder mouthpiece. The tubular element 60 can have different diameters depending on the dimensions of the drainage tubes to be introduced.

The tubular element 60 can be integrated in the main body 52. Advantageously, the tubular element 60 can be provided separately and then fixed to the rest of the main body 52 by adhesive bonding or heat-sealing. In this manner it is possible to adopt drainage tubes of different diameters simply by assembling a tubular element 60 having a different diameter.

The sliding body comprises an obturator or plunger element 64 which is longitudinally extended and is arranged at the distal portion of said sliding body. The obturator 64 is inserted within the cavity of the tubular element 60 of the main body 52. The obturator 64 can move, in particular it slides longitudinally, within the cavity of the tubular element 60 of the main body 52.

The obturator 64 comprises a cutting blade 68, which slides integrally is with the obturator 64 and is arranged and fixed at the distal end of said obturator 64. The cutting blade 68 passes through a passage slot arranged at the terminal 62 of the tubular element 60 of the main body 52. The cutting blade 68 is preferably made of stainless steel and is appropriately contoured. The obturator 64 comprises a stroke limiting disk 66, which is arranged and fixed at the proximal end of said obturator 64.

The sliding body comprises a longitudinally extended tubular body 70, which is arranged at the proximal portion of said sliding body. The tubular body 70 is inserted within the cavity of a tubular portion 58 of the main body 52. The tubular body 70 can move, in particular slides longitudinally, within the cavity of the tubular portion 58 of the main body 52. The tubular body 70 comprises a partition 72. The proximal face of the stroke limiting disk 66 of the obturator 64 is engaged on the distal face of the partition 72.

The sliding carriage 56 comprises a rotating mechanism 74, which is adapted to load and release the sliding body, i.e., the obturator 64 and the tubular body 70. The rotating mechanism 74 comprises a first lever 76, a second lever 78 and a third lever 80. The rotating mechanism 74 is accommodated in the adapted central pivot, so as to not be able to exit, and its shape is such to allow only the rotations required to perform the operations described as follows.

The main body 52 comprises inside it the group of springs. The loading and release spring 82 is compressed by the longitudinal movement of the tubular body 70 which is integral with the sliding carriage 56, during the pressing of the latter by the physician, and then released by means of the rotating mechanism 74, causing the controlled exit of the cutting blade 68 through the passage slot of the terminal 62, by an extent that is limited by the stroke limiting elements 94 and 96. The loading and release spring 82 is engaged, at one end, on a pivot which is arranged in the distal face of the lid 54 and, at the other end, on the proximal face of the partition 72 of the tubular body 70.

The return and positioning spring 84 is adapted to return the cutting blade 68 to a retracted position within its own seat (initial "rest" or safety position), following the controlled exit of said cutting blade 68 through the passage slot of the terminal 62. The return and positioning spring 84 is engaged, at one end, on the distal face of the stroke limiting disk 66 of the obturator 64 and, at the other end, on the proximal face of the tubular portion 58 of the main body 52.

The preloading and return spring 86 is adapted to return to an extended position the siding carriage 56, thus returning it to its initial position, following the pressing and subsequent release of the latter on the part of the physician. The preloading and return spring 86 is engaged, at one end, on a pivot arranged in the distal face of the lid 54 and, at the other end, on a pivot arranged in the proximal face of the sliding carriage 56.

With reference to FIGS. 6 to 10, the operation of the second embodiment (with snap insertion) of the percutaneous introducer, particularly for flexible drainage tubes and with various profiles, according to the disclosure, designated generally by the reference numeral 50, is described as follows.

In order to create the percutaneous access by means of the percutaneous introducer 50, initially the terminal 62 of the tubular element 60 of the main body 52 is arranged in contact with the skin of the patient, at the insertion site prepared previously by creating the conditions of sterility and local anesthesia.

The physician applies a slight pressure, pressing with the index or middle finger on the sliding carriage 56 and making it slide toward the inside of the main body 52. The sliding carriage 56, by retracting, compresses the preloading and return spring 86. The sliding carriage 56 entrains integrally the tubular body 70 of the sliding body, in particular by means of the first lever 76 of the rotating mechanism 74, which engages a rib 88 of the tubular body 70. The tubular body 70 of the sliding body, by retracting, compresses the loading and release spring 82, while the distal face of the stroke limiting disk 66 of the obturator 64 loses contact with the corresponding end of the return and positioning spring 84.

When the sliding carriage 56 and the tubular body 70 have arrived proximate to the stroke limit, the second lever 78 of the rotating mechanism 74 strikes a first rib 90 of the lid 54, which causes a rotation of the rotating mechanism 74. This rotation of the rotating mechanism 74 releases the tubular body 70, which is consequently pushed toward the initial position by the loading and release spring 82.

Due to the balancing of the mutual forces of the loading and release spring 82 and of the return and positioning spring 84, the tubular body 70 acquires a potential energy which, being in contact with the obturator 64 by means of the stroke limiting disk 66, causes said obturator 64 to slide forward toward the skin of the patient.

The energy is such that the obturator 64 accompanies integrally the cutting blade 68, making it exit for a short extent through the passage slot of the terminal 62, cutting the skin and/or the muscle bundles. The extent of the exit of the cutting blade 68 is limited by one or both stroke limiting elements 94 and 96 of the cylindrical body 70 and of the obturator 64, respectively.

The advancement movement of the tubular body 70 of the sliding body compresses the return and positioning spring 84, which therefore returns the cutting blade 68 to the retracted position inside its own seat (initial "rest" or safety position) directly after the exit of the cutting blade 68. In this manner, a single very quick and shallow "shot" is obtained which allows to cut the tissue that are in front of the percutaneous introducer 50 only following a voluntary act of the physician and without the risk of involuntary damage of the internal organs.

At this point the physician can release the sliding carriage 56, which is returned to its initial position by the preloading and return spring 86. During the retraction stroke of the sliding carriage 56, the rotating mechanism 74 remains in the rotated position by virtue of the calibrated friction with the corresponding central pivot; this allows the first lever 76 of the rotating mechanism 74 to move beyond the rib 88 of the tubular body 70 without interference. Before reaching the stroke limit, the second lever 78 of the rotating mechanism 74 strikes a second rib 92 of the lid 54, which causes a further rotation of the rotating mechanism 74 in the opposite direction with respect to the preceding rotation, returning it to the initial position.

As mentioned, the described operation allows to obtain a single "short", which performs a calibrated cutting of the tissues that are in front of the percutaneous introducer 50, in particular in contact with the terminal 62 of the tubular element 60. The cut allows the percutaneous introducer 50 to penetrate by a certain extent through the thoracic or abdominal wall of the patient without the need for further accessories and without having to apply excessive pressure.

The "shot" can be repeated several times at the physician's discretion: whenever the physician encounters a certain resistance to the introduction of the device, he can use a "shot" to cut the underlying tissues and continue the stroke without resistance. Once the percutaneous access has been created, the physician can proceed with the insertion of the surgical drainage tube and with subsequent fixation.

The percutaneous introducer 10, 50 according to the disclosure is adapted for ambidextrous use and therefore can be used equally by right-handed or left-handed physicians.

The percutaneous introducer 10, 50 according to the disclosure is immediately ready for use, without requiring other accessories for its use besides the normal preparation of the sterile insertion site.

The difference between the embodiment of the percutaneous introducer 10 with manual insertion and the embodiment of the percutaneous introducer 50 with snap insertion resides in that in the first case the exit of the cutting blade is controlled directly by the physician, who decides the duration of the cutting action and the moment when to make it retract, while in the second case the action of the sliding carriage and of the group of springs predetermines the cutting action, which is swift and sudden. In practice, in the second case the physician only decides the moment when to perform the "shot".

Advantageously, once the percutaneous access has been created by means of the percutaneous introducer 10, 50 according to the disclosure, the physician can use a retention and positioning device or, for brevity, positioning device 100, 110 to insert the surgical drainage tube in the chest of the patient.

In particular, the positioning device 100, 110 is configured to guide the insertion of the surgical drainage tube made of flexible material through the previously created percutaneous access.

In order to be able to insert a surgical drainage tube, particularly if it is made of highly flexible material, such as for example medical silicone, it is necessary to give it a sufficient rigidity, so that it can be inserted easily in the percutaneous access created by means of the percutaneous introducer 10, 50.

In practice, the physician must have the possibility to insert the surgical drainage tube, easily extract the positioning device, and end the positioning according to clinical requirements.

Within the scope of the present disclosure, a kit for the introduction of drainage tubes comprises a percutaneous introducer 10, 50 and a longitudinally extended positioning device 100, 110.

Figure 11:
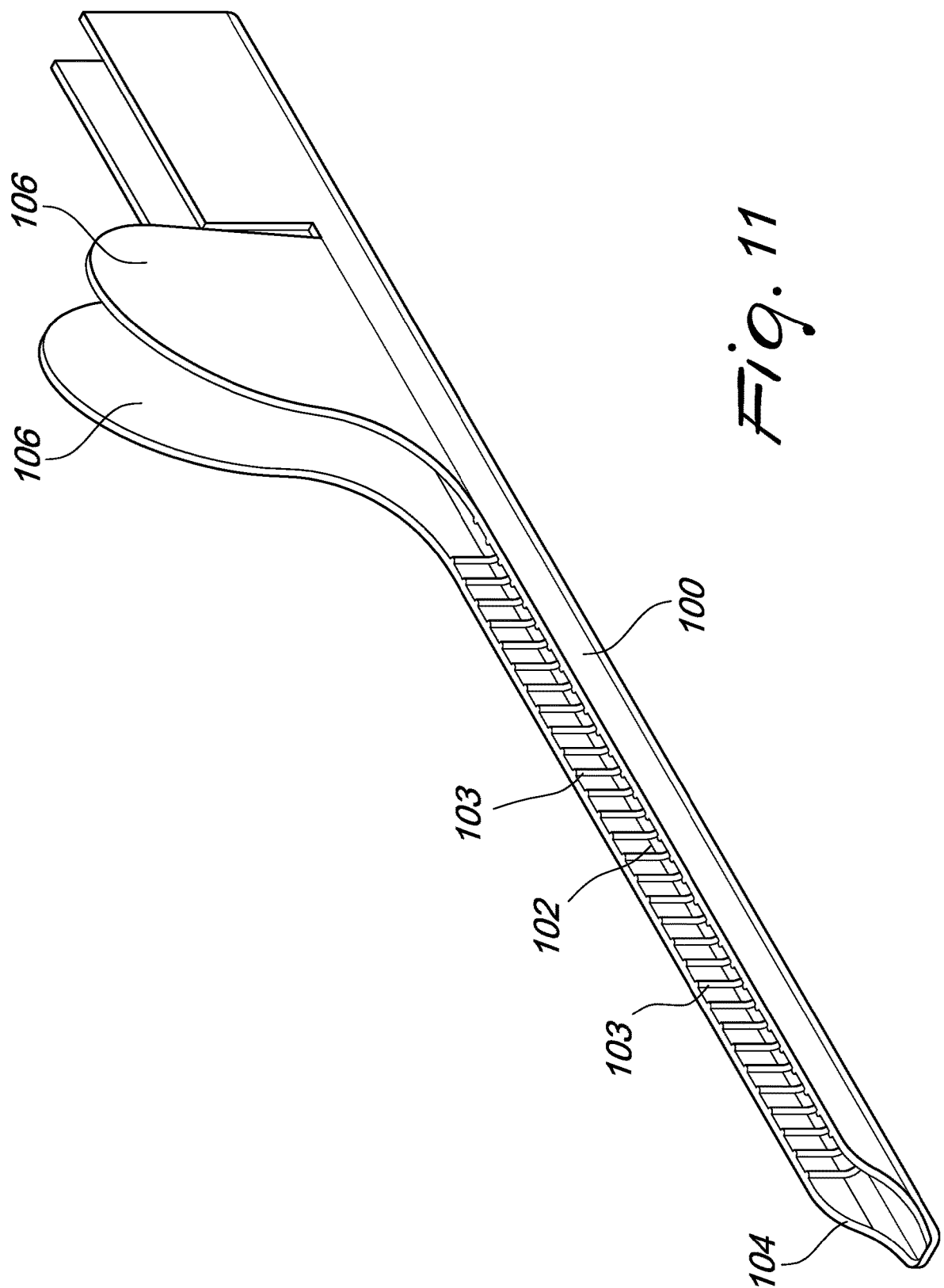
FIG. 11 is a perspective view of a first embodiment of the retention and positioning device, according to the present disclosure.

With reference to FIG. 11, in a first embodiment the positioning device 100 is a longitudinally extended monolithic body, which comprises a longitudinally extended seat or channel 102 which is open upward and is substantially equal in length to said positioning device 100. The seat 102 is adapted to accommodate a surgical drainage tube. The dimensions of the seat 102, and therefore of the positioning device 100, vary as a function of the diameter of the surgical drainage tube that must be positioned. The seat 102 comprises a plurality of raised portions 103, which are preferably linear and U-shaped and are arranged along the internal surface of said seat 102.

The surgical drainage tube is inserted by the physician in the seat 102 so that the distal terminal portion of said surgical drainage tube remains included within said seat 102.

The positioning device 100 comprises a pair of flexible wings 106; the physician, after inserting the surgical drainage tube, compresses these wings 106, thus retaining said surgical drainage tube within the seat 102. The flexibility of the wings 106 can be imparted by means of a longitudinal slot which is arranged at the base of said wings 106, in the region between them and the seat 102.

The positioning device 100 comprises a terminal 104, which preferably has a conical tip and is arranged at a distal end of said positioning device 100 and therefore of the seat 102. The distal terminal 104 is configured to facilitate the insertion of the positioning device 100 within the percutaneous access.

The operation of the first embodiment of the position 100, of the monolithic type, is described as follows.

Initially, the physician inserts the surgical drainage tube within the seat 102 of the positioning device 100, which is chosen according to the diameter of said tube, so that the terminal portion of said surgical drainage tube remains included within said seat 102.

The physician compresses the adapted flexible wings 106 of the positioning device 100, thus retaining the surgical drainage tube firmly within the seat 102. Then the physician proceeds with the insertion of the positioning device 100 within the percutaneous access created by means of the percutaneous introducer 10, 50. The insertion operation is facilitated by the distal terminal 104, which preferably has a conical tip, of the positioning device 100.

Once the surgical drainage tube has been partially inserted in the percutaneous access, it is possible to remove the positioning device 100, releasing the pressure on the flexible wings 106 and extracting it from the percutaneous access.

Finally, the physician proceeds with the complete insertion of the surgical drainage tube and with its subsequent fixation.

If needed, the positioning device 100 can be extracted only partially and then, by again pressing on the flexible wings 106, it is possible to achieve a further insertion of the surgical drainage tube in the percutaneous access of the wound.

Figure 12:
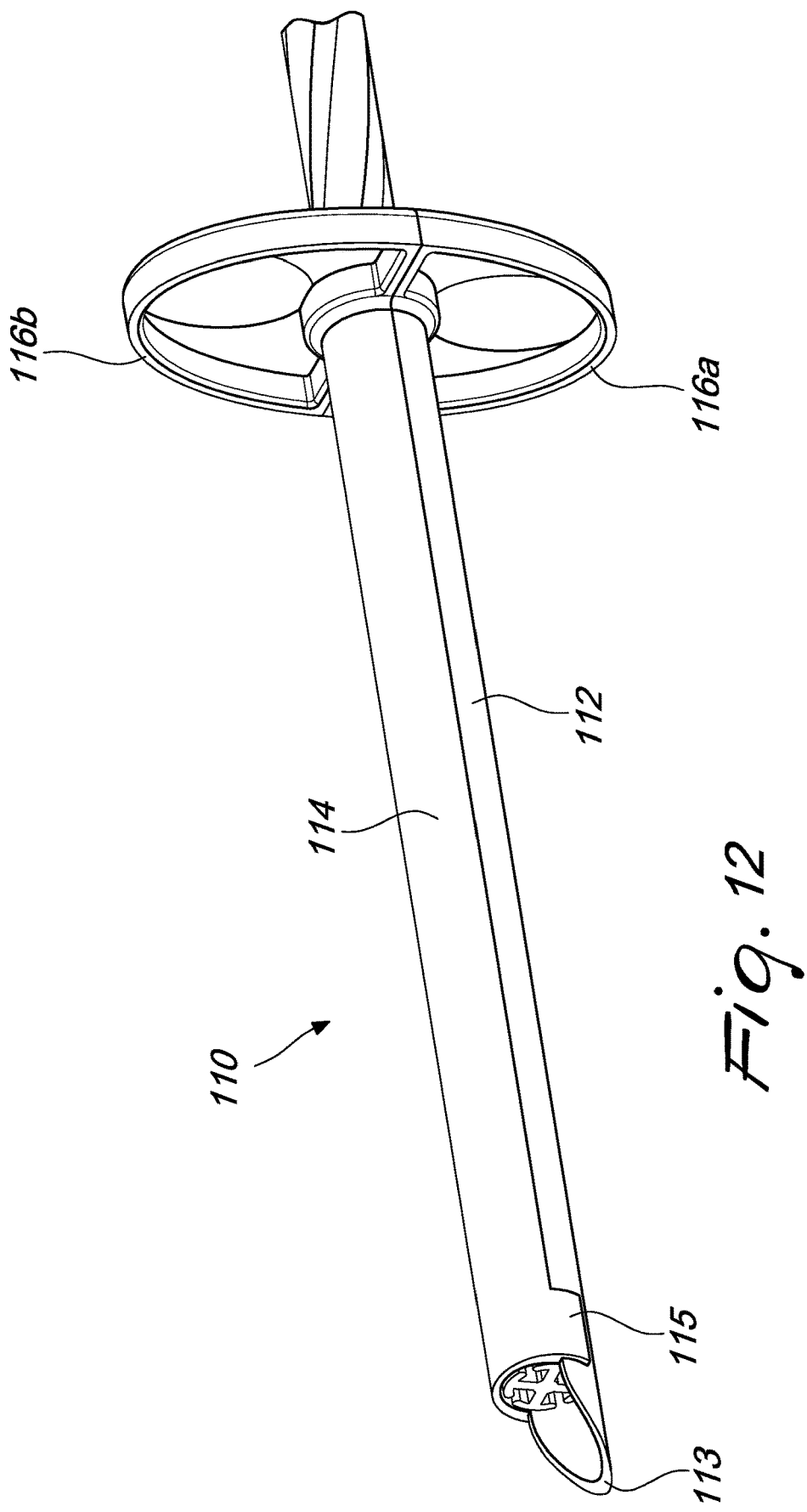
FIG. 12 is a perspective view of a second embodiment of the retention and positioning device, according to the present disclosure.

With reference to FIG. 12, in a second embodiment the positioning device 110 is of the clam shell type, comprising a lower half-shell body 112 and an upper half-shell body 114, both of which are longitudinally extended and must be assembled and coupled to each other.

The coupling between the lower half-shell body 112 and the upper half-shell body 114 creates inside them a seat or channel which is longitudinally extended, is closed and is substantially equal in length to said positioning device 110. The seat is adapted to accommodate a surgical drainage tube. The dimensions of this seat, and therefore of the lower half-shell body 112 and of the upper half-shell body 114 of the positioning device 110, vary as a function of the diameter of the surgical drainage tube that must be positioned.

The surgical drainage tube is inserted by the physician in the seat located between the lower half-shell body 112 and the upper half-shell body 114 so that the distal terminal portion of said surgical drainage tube remains included within said seat.

The lower half-shell body 112 comprises a terminal 113, which preferably has a conical tip and is arranged at a distal end of said lower half-shell body 112, and therefore of the positioning device 110. The distal terminal 113 is configured to facilitate the insertion of the positioning device 110 within the percutaneous access.

The upper half-shell body 114 comprises a pair of front pins 115, preferably arranged at a distal end of said upper half-shell body 114, which are adapted to lock said upper half-shell body 114 to the lower half-shell body 112, engaging in corresponding recesses provided in the lower half-shell body 112.

The positioning device 110 furthermore comprises a pair of rear pins (not shown), also adapted to mutually lock the lower half-shell body 112 and the upper half-shell body 114.

The positioning device 110 comprises a pair of wings, in particular a first wing 116a arranged at a proximal end of the lower half-shell body 112 and a second wing 116b which is arranged at a proximal end of the upper half-shell body 114. The wings 116a and 116b are configured to separate or uncouple the two half-shell bodies 112 and 114 and to extract the positioning device 110, in particular the respective half-shell bodies 112 and 114, from the percutaneous access.

The operation of the second embodiment of the positioning device 100 of the clam shell type, is described as follows.

Initially the physician grips the lower half-shell body 112 and arranges thereat the surgical drainage tube to be inserted, taking care to keep the terminal portion of said drainage tube inside the seat, without making it protrude beyond the distal terminal 113 of said lower half-shell body 112. Then the physician mates the upper half-shell body 114 with the lower half-shell body 112, interlocking it by using the pair of front pins 115 and the pair of rear pins.

Once the coupling has been performed, this produces a rigid positioning device 110, which keeps the surgical drainage tube properly positioned while the physician introduces it in the percutaneous access, previously obtained by means of the percutaneous introducer 10, 50, until it penetrates for approximately two thirds of its length.

Keeping the surgical drainage tube stationary, the physician can easily disengage the rear pins by pressing with the thumb against the wing 116a of the lower half-shell body 112, to then separate or uncouple the two half-shell bodies 112 and 114, and finally extract from the percutaneous access the upper half-shell body 114, gripping the wing 116b thereof.

At this point the physician can extract from the percutaneous access also the lower half-shell body 112, retaining the surgical drainage tube with one hand and extracting the lower half-shell body 112 with the other hand.

At the end, the physician can optionally insert the surgical drainage tube by another extent, according to the clinical requirements: since it has already penetrated through the percutaneous access, the sliding of the surgical drainage tube is very easy and can be performed without any aid.

In practice it has been found that the disclosure achieves fully the intended aim and advantages. In particular it has been shown that the percutaneous introducer, particularly for flexible drainage tubes and with various profiles, thus conceived allows to overcome the quality limitations of the background art, since it allows both the creation of a percutaneous access in a simple, safe and economical manner, and the introduction and correct positioning of drainage tubes having different profiles and made of different materials.

One advantage of the percutaneous introducer, particularly for flexible drainage tubes and with various profiles, according to the present disclosure, resides in that it allows access through the skin and to the underlying tissues, in particular through the thoracic wall, by means of a blade that is always protected and the cutting action of which is clearly determined (exit time and depth are always controlled) and always constant. In particular, in the version with snap insertion, the cutting action is predetermined, since the physician decides when to perform the "shot" but every repetition is always identical, and therefore the cutting action is independent of the dexterity and skill of the physician.

Another advantage of the percutaneous introducer, particularly for flexible drainage tubes and with various profiles, according to the present disclosure, resides in that there is no dilation of the created percutaneous access, since the latter is created by choosing an introducer that is adequate for the diameter of the surgical drainage tube and therefore it is not necessary to perform any effort during the positioning of the surgical drainage tube.

A further advantage of the percutaneous introducer, particularly for flexible drainage tubes and with various profiles, according to the present disclosure, resides in that it is not necessary to apply any intense pressure during entry through the thoracic or abdominal wall. It is in fact sufficient to keep the end of the introducer in contact, press slightly, and then perform a cutting action in order to open a minimal passage through the tissues. The operation can be repeated at will up to the complete entry in the chest or abdomen.

Another advantage of the percutaneous introducer, particularly for flexible drainage tubes and with various profiles, according to the present disclosure, resides in that it is not subject to the risk of accidental damage to patients caused by unprotected sharp objects. In fact, except during the voluntary cutting action of the physician, the blade is always in the retracted position and is kept thereat by an adapted spring.

A further advantage of the percutaneous introducer, particularly for flexible drainage tubes and with various profiles, according to the present disclosure, resides in that it can be used to insert drainage tubes having multiple diameters, profiles and/or different materials. In particular, the structure of the introducer is such that it is particularly suitable for the positioning of drainage tubes with profiles other than the tubular one (for example a flat profile, a splined profile, etc.) and made of soft and nontraumatic materials (for example medical silicone).

Another advantage of the percutaneous introducer, particularly for flexible drainage tubes and with various profile's according to the present disclosure, resides in that it allows to use the same method to introduce different types of drainage tubes and in any clinical situation (for example emergency, post-surgical treatment, etc.). Therefore, medical personnel no longer needs to learn different methods, to the full advantage of the safety of the patient and of the physician.

Another advantage of the percutaneous introducer, particularly for flexible drainage tubes and with various profiles, according to the present disclosure, resides in that it is adapted to be used in any clinical situation and most of all does not require personnel that is specialized and/or belongs to the surgical area, by virtue of the uniqueness and the simplicity of the positioning operations, together with independence from dexterity of the operator.

Although the percutaneous introducer according to the disclosure has been conceived in particular for the introduction in organic tissues of flexible thoracic drainage tubes and with various profiles, it can in any case be used more generally for the introduction in organ tissues of drainage tubes of any type, profile and/or size.

The disclosure thus conceived is susceptible of numerous modifications and variations, all of which are within the scope of the appended claims. All the details may further be replaced with other technically equivalent elements.

In practice, the materials used, so long as they are compatible with the specific use, as well as the contingent shapes and dimensions, may be any according to the requirements and the state of the art.

To conclude, the scope of the protection of the claims must not be limited by the illustrations or preferred embodiment shown in the description by way of example, but rather the claims must comprise all the characteristics of patentable novelty that reside in the present disclosure, including all the characteristics that would be treated as equivalents by the person skilled in the art.

The disclosures in Italian Patent Application No. 102018000001649 from which this application claims priority are incorporated herein by reference.

The invention claimed is:

1. A percutaneous introducer comprising:
a main body comprising a longitudinally extended tubular element arranged in the distal portion of said main body, said longitudinally extended tubular element comprising a terminal arranged at a distal end of said longitudinally extended tubular element;
a sliding body comprising a longitudinally extended obturator arranged in a distal portion of said sliding body, said longitudinally extended obturator being inserted and being movable longitudinally within said longitudinally extended tubular element of said main body, said longitudinally extended obturator comprising a cutting blade arranged and fixed at a distal end of said longitudinally extended obturator; and
a return and positioning spring adapted to return said cutting blade to a retracted position within its seat, following a controlled exit of said cutting blade through a passage slot arranged in said terminal of said longitudinally extended tubular element, an advancement movement of the sliding body compressing the return and positioning spring, which returns the cutting blade to the retracted position within its own seat as soon as a physician releases a pusher pin of the sliding body.

2. The percutaneous introducer according to claim 1, wherein said main body comprises a ring arranged in a proximal portion of said main body, said ring being associated with a proximal end of said longitudinally extended tubular element.

3. The percutaneous introducer according to claim 2, wherein said main body comprises a wing associated with said ring and being arranged on an opposite side with respect to said longitudinally extended tubular element.

4. The percutaneous introducer according to claim 1, wherein said sliding body comprises said pusher pin arranged in a proximal portion of said sliding body and associated with a proximal end of said obturator.

5. The percutaneous introducer according to claim 1, further comprising a lid adapted to close a first opening of said main body which is arranged in a proximal face of said main body.

6. The percutaneous introducer according to claim 4, wherein said sliding body comprises a longitudinally extended tubular body arranged in the proximal portion of said sliding body, said longitudinally extended tubular body being inserted and movable longitudinally within a tubular portion of said main body.

7. The percutaneous introducer according to claim 6, wherein said longitudinally extended tubular body comprises a partition, a proximal end of said longitudinally extended obturator being engaged on a distal face of said partition.

8. The percutaneous introducer according to claim 5, further comprising a sliding carriage disposed in a second opening of said main body arranged in a distal face of said main body, said sliding carriage being longitudinally movable within said main body, said sliding carriage comprising a rotating mechanism engaged on a rib of said tubular body and is adapted to load and release said sliding body.

9. The percutaneous introducer according to claim 8, wherein said main body comprises a loading and release spring adapted to be compressed by said tubular body integral with said sliding carriage and then released by means of said rotating mechanism, causing said controlled exit of said cutting blade.

10. The percutaneous introducer according to claim 9, wherein said loading and release spring is engaged, at one end, on a pivot arranged in the distal face of said lid and, at the other end, on the proximal face of said partition of said tubular body.

11. The percutaneous introducer according to claim 8, wherein said main body comprises a preloading and return spring adapted to return said sliding carriage to the extended position.

12. The percutaneous introducer according to claim 11, wherein said preloading and return spring is engaged, at one end, on a pivot arranged in the distal face of said lid and, at the other end, on a pivot arranged in the proximal face of said sliding carriage.

13. The percutaneous introducer according to claim 1, wherein said terminal of said longitudinally extended tubular element is shaped like a recorder mouthpiece.

14. A kit for inserting surgical drainage tubes, comprising a percutaneous introducer comprising a main body comprising a longitudinally extended tubular element arranged in the distal portion of said main body, said longitudinally extended tubular element comprising a terminal arranged at a distal end of said longitudinally extended tubular element; a sliding body comprising a longitudinally extended obturator arranged in a distal portion of said sliding body, said longitudinally extended obturator being inserted and being movable longitudinally within said longitudinally extended tubular element of said main body, said longitudinally extended obturator comprising a cutting blade arranged and fixed at a distal end of said longitudinally extended obturator; and a return and positioning spring adapted to return said cutting blade to a retracted position within its seat, following a controlled exit of said cutting blade through a passage slot arranged in said terminal of said longitudinally extended tubular element, and a longitudinally extended positioning device configured to guide an insertion of a surgical drainage tube through a percutaneous access, wherein said longitudinally extended positioning device is a longitudinally extended monolithic body having a longitudinally extended seat open upward for the accommodation of said surgical drainage tube, said seat comprising a plurality of raised portions arranged along its internal surface, a pair of flexible wings configured to retain said surgical drainage tube within said seat, and a distal terminal configured to facilitate the insertion of said positioning device inside said percutaneous access.

15. The kit for inserting surgical drainage tubes according to claim 14, wherein said longitudinally extended positioning device comprises a lower half-shell body and an upper half-shell body, both of which are longitudinally extended, a coupling between said lower half-shell body and said upper half-shell body creating a longitudinally extended seat which is closed for the accommodation of said surgical drainage tube, said lower half-shell body and said upper half-shell body comprising respective wings configured to separate or uncouple said half-shell bodies and to extract said longitudinally extended positioning device from said percutaneous access, said lower half-shell body comprising a distal terminal configured to facilitate an insertion of said longitudinally extended positioning device within a percutaneous access.

16. A percutaneous introducer comprising:
- a main body comprising a longitudinally extended tubular element arranged in the distal portion of said main body, said longitudinally extended tubular element comprising a terminal arranged at a distal end of said longitudinally extended tubular element;
- a sliding body comprising a longitudinally extended obturator arranged in a distal portion of said sliding body, said longitudinally extended obturator being inserted and being movable longitudinally within said longitudinally extended tubular element of said main body, said longitudinally extended obturator comprising a cutting blade arranged and fixed at a distal end of said longitudinally extended obturator; and
- a return and positioning spring adapted to return said cutting blade to a retracted position within its seat, following a controlled exit of said cutting blade through a passage slot arranged in said terminal of said longitudinally extended tubular element, and further comprising a lid adapted to close a first opening of said main body which is arranged in a proximal face of said main body, and also further comprising a sliding carriage disposed in a second opening of said main body arranged in a distal face of said main body, said sliding carriage being longitudinally movable within said main body, said sliding carriage comprising a rotating mechanism engaged on a rib of said tubular body and is adapted to load and release said sliding body.

* * * * *